(12) United States Patent
Smith

(10) Patent No.: US 8,496,331 B2
(45) Date of Patent: Jul. 30, 2013

(54) PORTABLE PATTERN-GENERATING OPHTHALMIC PROBE

(75) Inventor: Ronald T. Smith, Irvine, CA (US)

(73) Assignee: Alcon Research, Ltd., Fort Worth, TX (US)

(*) Notice: Subject to any disclaimer, the term of this patent is extended or adjusted under 35 U.S.C. 154(b) by 0 days.

(21) Appl. No.: 13/208,496

(22) Filed: Aug. 12, 2011

(65) Prior Publication Data

US 2013/0038836 A1     Feb. 14, 2013

(51) Int. Cl.
*A61B 3/10* (2006.01)
*A61B 3/00* (2006.01)

(52) U.S. Cl.
USPC .......................................... 351/221; 351/246

(58) Field of Classification Search
USPC .................................. 351/200–246
See application file for complete search history.

(56) References Cited

U.S. PATENT DOCUMENTS

| | | | |
|---|---|---|---|
| 3,947,186 A | 3/1976 | Howland | |
| 4,423,931 A | 1/1984 | Shapiro | |
| 4,730,910 A | 3/1988 | Humphrey | |
| 4,738,521 A | 4/1988 | Volk | |
| 4,900,144 A | 2/1990 | Kobayashi | |
| 7,048,379 B2 | 5/2006 | Miller et al. | |
| 7,422,327 B2 | 9/2008 | Smith | |
| 7,566,173 B2 | 7/2009 | Auld et al. | |
| 7,618,177 B2 | 11/2009 | Cazzini | |
| 7,690,787 B2 * | 4/2010 | Koschmieder et al. | 351/216 |
| 2003/0169603 A1 * | 9/2003 | Luloh et al. | 362/574 |
| 2006/0170867 A1 | 8/2006 | Koschmieder et al. | |
| 2009/0182313 A1 | 7/2009 | Auld | |
| 2011/0110114 A1 | 5/2011 | Papac et al. | |
| 2011/0112377 A1 * | 5/2011 | Papac et al. | 600/249 |
| 2011/0122366 A1 * | 5/2011 | Smith | 351/221 |
| 2011/0141759 A1 | 6/2011 | Smith | |
| 2011/0144627 A1 | 6/2011 | Smith | |
| 2011/0144745 A1 | 6/2011 | Martin et al. | |

FOREIGN PATENT DOCUMENTS

| | | |
|---|---|---|
| EP | 1549205 B1 | 4/2012 |
| GB | 1454675 | 11/1976 |

OTHER PUBLICATIONS

Yadlowsky, Michael J., Combined Surgical Endoprobe for Optical Coherence Tomography, Illumination or Photocoagulation, U.S. Appl. No. 13/354,566, filed Jan. 20, 2012, 17 pages.
Smith, Ronald T., Laser Illumination System, U.S. Appl. No. 12/872,412, filed Aug. 31, 2020, 18 pages.
Prosecution History of U.S. Patent No. 7,422,327, filed Dec. 31, 2006, 142 pages.

* cited by examiner

*Primary Examiner* — Mohammed Hasan

(57) ABSTRACT

A pattern-generating intraocular probe is provided that includes a cannula including a diffractive optical element (DOE), the DOE being patterned such that an on-axis illumination of the DOE produces an emitted beam forming a linear pattern; and a handpiece connected to a proximal of the cannula.

20 Claims, 5 Drawing Sheets

PORTABLE PATTERN-GENERATING OPHTHALMIC PROBE

BACKGROUND OF THE INVENTION

Ophthalmic illuminators allow a physician to illuminate the interior structure of the eye such as the vitreous and the retina during medical procedures. For example, an endoscopic ophthalmic illuminator (endo-illuminator) includes an optical fiber within the bore of a cannula. By driving a proximal of the optical fiber with a suitable light source, light emitted from a distal of the fiber illuminates the desired portion of the eye during a surgical procedure. Alternatively, a physician may illuminate the eye with fiber optic illumination while using an ophthalmic microscope.

A specialized ophthalmic illumination procedure has been developed to determine retinal fundus topography information. For example, a fundus camera has been configured to include a diffractive optical element (DOE) that projects a grid or line pattern onto the retina. To simplify the optical configuration, fundus lenses have been developed such as disclosed in U.S. Pat. No. 7,422,327 that include a volume hologram DOE that is illuminated off-axis. Such a DOE would thus be relatively transparent to the remaining on-axis optical lenses in the fundus camera. However, the off-axis illumination and the addition of the DOE lens still introduces some complexity for a fundus camera.

Accordingly, there is a need in the art for an improved ophthalmic illumination for retinal topography determinations.

SUMMARY OF THE INVENTION

In accordance with a first aspect of the disclosure, a pattern-generating intraocular probe is provided that includes a cannula including a diffractive optical element (DOE), the DOE being patterned such that an on-axis illumination of the DOE produces an emitted beam forming a linear pattern; and a handpiece connected to a proximal of the cannula.

In accordance with a second aspect of the disclosure, a method is provided that includes inserting a cannula into an eye, wherein the cannula includes a diffractive optical element (DOE) patterned such that an on-axis illumination of the DOE produces an emitted beam forming a linear pattern; and illuminating the DOE through a lumen of the cannula so as to produce the on-axis illumination such that the emitted beam forms the linear pattern on a retinal fundus.

In accordance with a third aspect of the invention, an intraocular probe is provided that includes a handpiece; a needle having a proximal connected to the handpiece; and a diffractive optical element (DOE) sealing a distal of the needle, the DOE being patterned to project a plurality of parallel lines onto a retina.

These and other aspects, forms, objects, features, and benefits of the present invention will become apparent from the following detailed drawings and description.

BRIEF DESCRIPTION OF THE DRAWINGS

In the accompanying drawings, which are incorporated in and constitute a part of the specification, embodiments of the invention are illustrated, which, together with a general description of the invention given above, and the detailed description given below, serve to exemplify the embodiments of this invention.

DETAILED DESCRIPTION OF THE INVENTION

Figure 1:
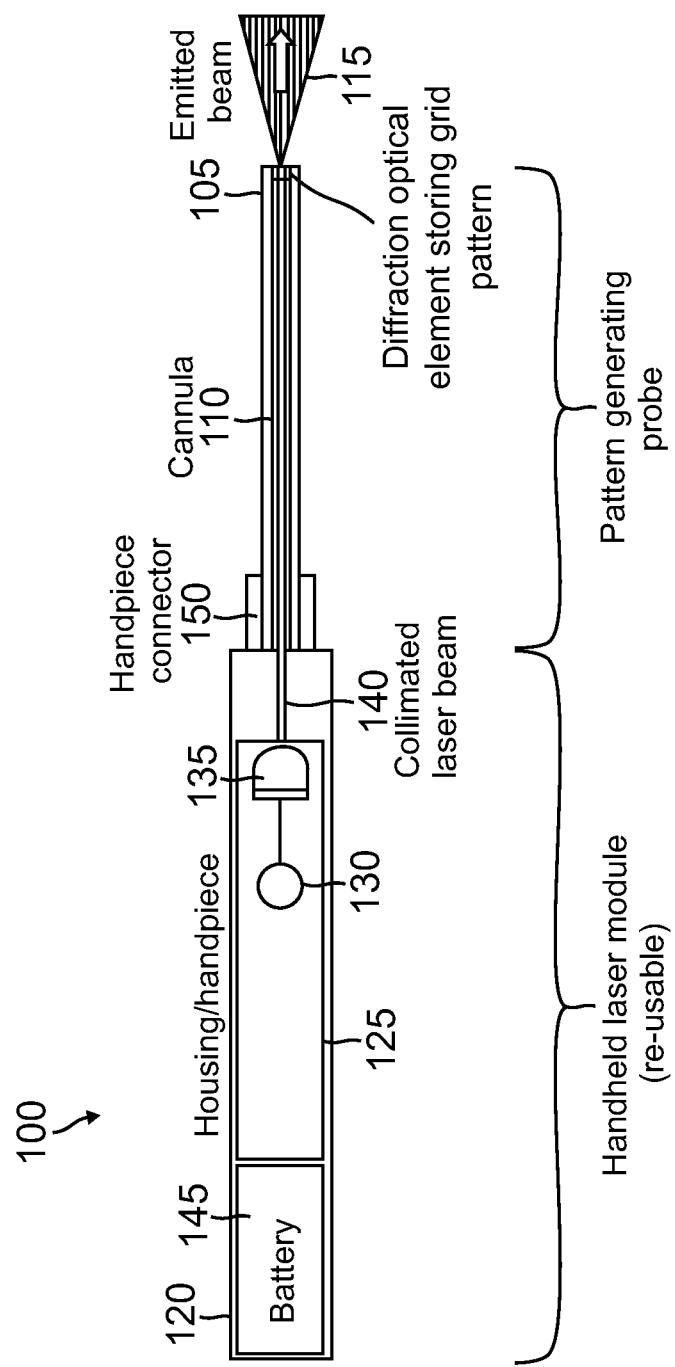
FIG. 1 is a cross-sectional view of an intraocular pattern-projecting probe for determining retinal topography.

The present disclosure relates generally to the field of ophthalmic medicine, and more particularly to devices and methods for determining retinal topography. For the purposes of promoting an understanding of the principles of the invention, reference will now be made to embodiments or examples illustrated in the drawings, and specific language will be used to describe these examples. It will nevertheless be understood that no limitation of the scope of the invention is thereby intended. Any alteration and further modifications in the described embodiments, and any further applications of the principles of the invention as described herein are contemplated as would normally occur to one skilled in the art to which the disclosure relates.

To provide an improved ability for retinal topography determination, an intraocular probe 100 is provided that includes an on-axis diffractive optical element 105 as shown in FIG. 1. A cannula or needle 110 includes diffractive optical element 105 at a distal to allow an emitted beam 115 projected by diffractive optical element 105 to properly diverge to illuminate the retinal field. A handpiece piece 120 includes a laser projector 125 having a laser source 130 driving collimating optics 135. Laser projector 125 is aligned with a lumen of cannula 105 so that a resulting collimated laser beam 140 emitted from collimating optics 135 travels longitudinally through the lumen to orthogonally (on-axis) intersect with diffractive optical element 105. Handpiece 120 includes a battery 145 to power laser source 130 such as a green laser diode. Other color sources may also be used. Diffractive optical element 105 hermetically seals the distal of cannula 105 to prevent fluids such as balanced saline solution from flooding cannula 105 and affecting laser source 130 and other components.

Figure 2:
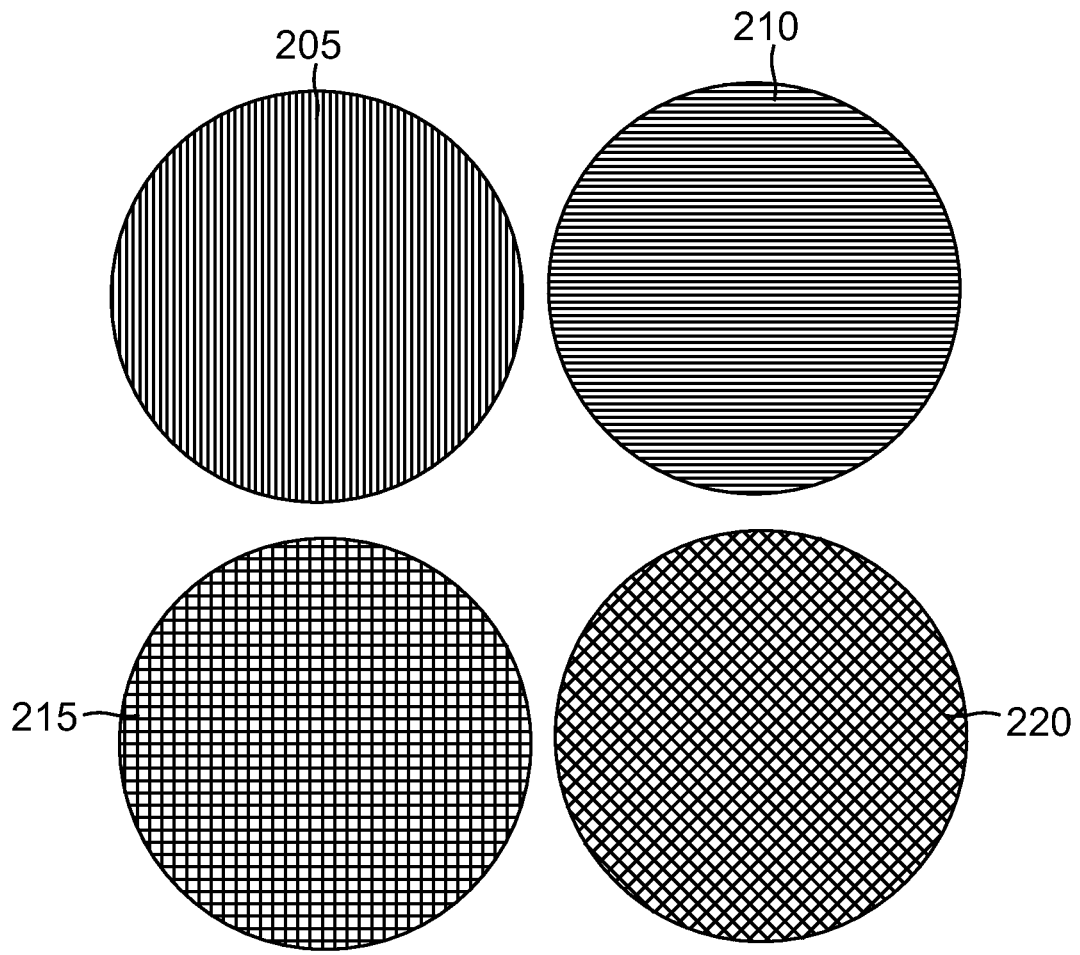
FIG. 2 illustrates several example projected patterns for the probe of FIG. 1.

As known in the diffractive optical arts, diffractive optical element 105 includes an etched planar surface that forms complex microstructures. By proper configuration of the resulting microstructures, a designer can tune a diffractive optical element to project virtually an infinite variety of patterns. With regard to determining retinal topography, the desired pattern includes one or more pluralities of parallel lines. If diffractive optical element 105 is configured to project a single plurality of parallel lines, emitted beam 115 will form a pattern such as patterns 205 or 210 in FIG. 2. Alternatively, if diffractive optical element 105 is configured to form two pluralities of orthogonally-oriented parallel lines, emitted beam 115 will form grid patterns such a patterns 215 and 220.

Figure 3:
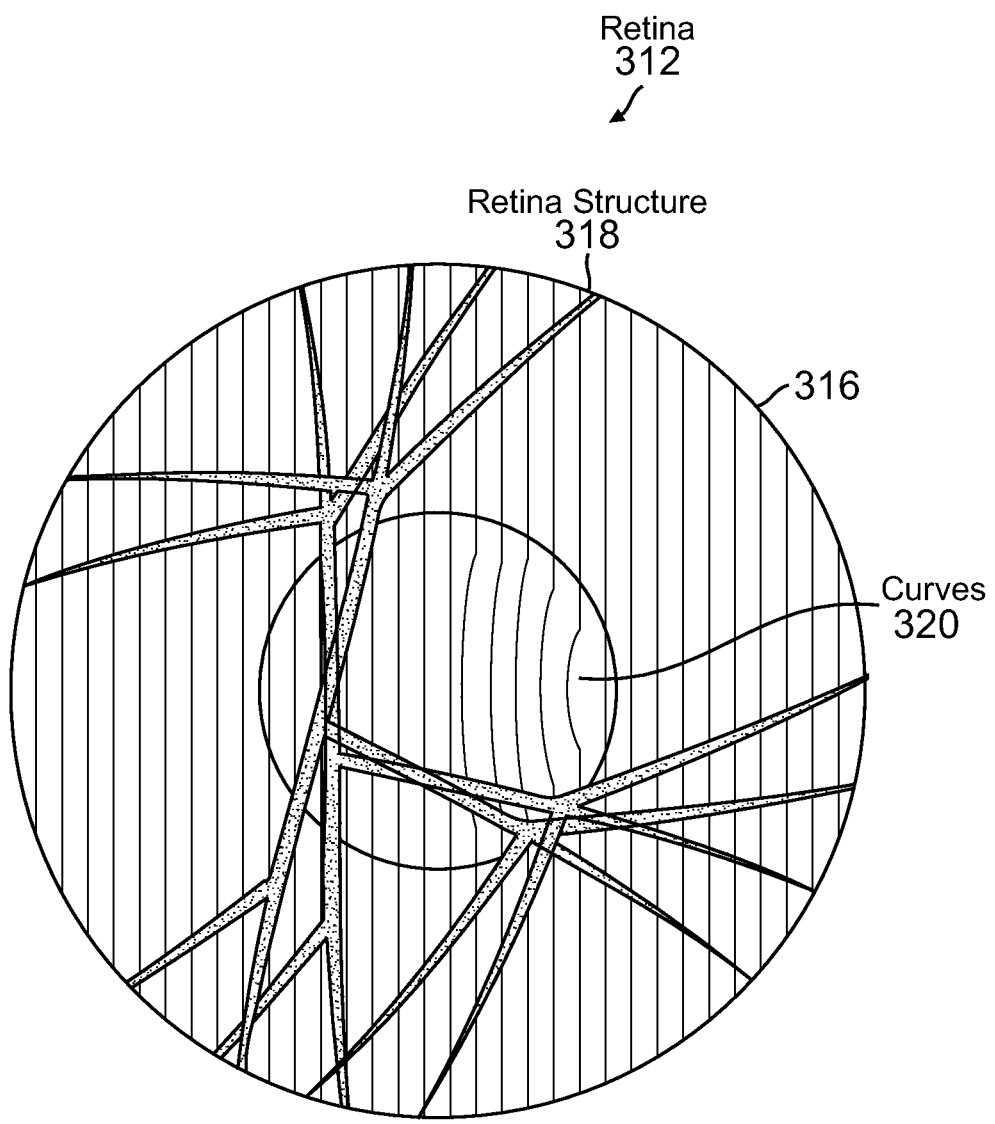
FIG. 3 shows how pathologies causing bumps or depressions in the retinal fundus distort the linear patterns projected by the probe of FIG. 1.

An example projected pattern on a retinal fundus 312 is shown in FIG. 3. The projected pattern illuminates retina structure 318. As discussed above, the off-axis illumination of fundus 312 maintains the linearity of parallel lines 316. However, a bump such as resulting from a retinal pathology causes curves 320. A surgeon may directly observe such irregularities or they may be imaged and studied off line using a fundus camera.

Figure 4:
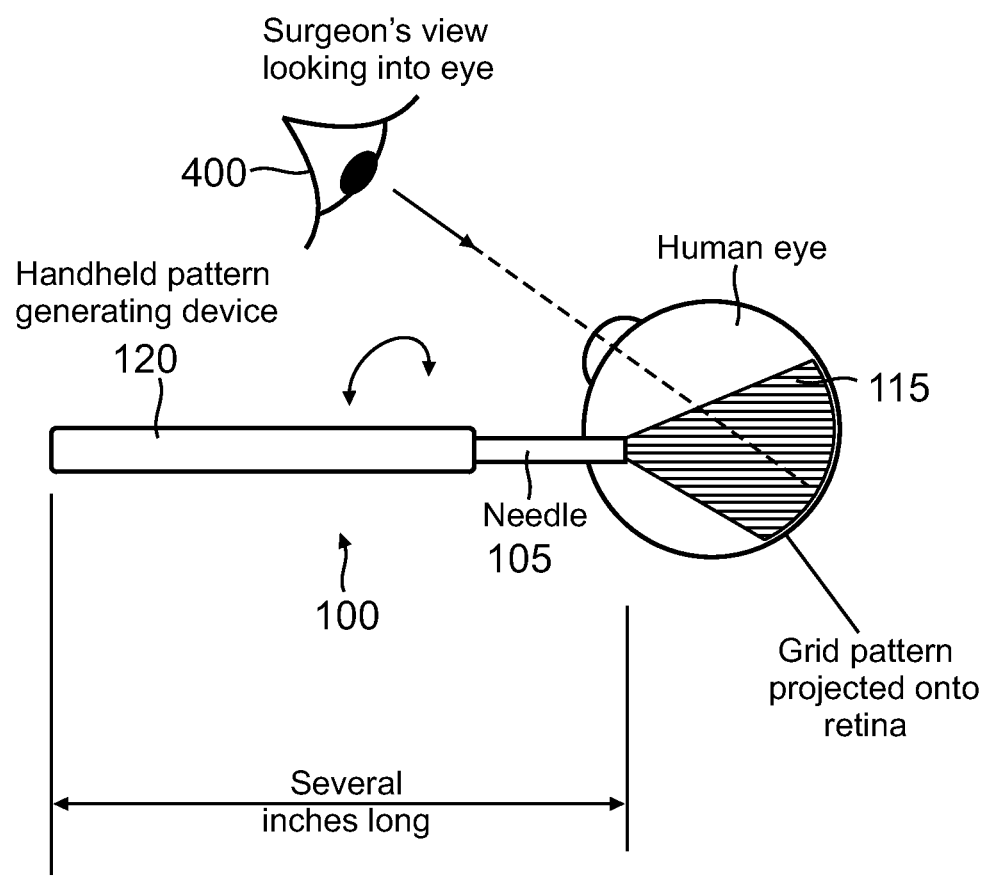
FIG. 4 is a view of the probe of FIG. 1 projecting its linear pattern onto a retina as manipulated by a clinician.

To illuminate a retinal fundus to determine its topography, a clinician may first use a trocar to pierce the sclera. The trocar is directed so as to place a trocar cannula providing access to the eye's interior at an angle that is off-axis with regard to the retina. As seen in FIG. 4, the clinician may grasp handpiece 120 so as to maneuver cannula 105 through the trocar cannula (not illustrated) to project diverging beam 115 onto the retinal fundus. Because the projected pattern is incident at an angle relative to the fundus perpendicular, any bumps or depressions in the retinal surface will result in curvature of the lines in the projected pattern. A clinician 400 (or a fundus camera) has an on-axis view through the eye's pupil at the illuminated fundus. Since probe 100 need only be several inches long, it is convenient for a clinician to place probe 100 so as to project the desired pattern onto the retina. Moreover, the clinician need merely rotate handpiece 120 about its longitudinal axis to rotate the resulting pattern. For example, if the handpiece is rotated 90 degrees, pattern 205 of FIG. 2 becomes pattern 210. Alternatively, probe 100 may include a slide lever (not illustrated) that rotates cannula 110 and DOE 105 relative to handpiece 120.

As compared to modifications of fundus lenses such as disclosed in U.S. Pat. No. 7,422,327, probe 100 may be made relatively inexpensively in that cannula 110 may be readily disconnected from handpiece 120 through operation of connector 150 as shown in FIG. 1. The remaining handpiece 120 is thus reusable such that cannula 110 and its diffractive optical element 105 may be readily removed and discarded after a medical procedure. Moreover, unlike fundus camera approaches, emitted beam 115 is not projected through the eye's pupil but instead is properly projected off-axis as shown in FIG. 4. In addition, cannula 105 needs no optical fiber to guide collimated beam 140 towards diffractive optical element 105. In general, propagation through an optical fiber will tend to introduce perturbations because of corresponding perturbations in refractive index of the fiber core. Such perturbations may then cause the projected linear pattern to become diffused.

Because diffractive optical element 105 is illuminated on-axis, its construction is less expensive as compared to the volume holography necessary for diffractive optical elements designed to receive off-axis illumination. In that regard, diffractive optical element 105 may be readily patterned using a computer-generated calculation of the fringe spacing and orientation to form the microstructure on the planar surface of diffractive optical element 105. This spacing and orientation results in the desired plurality (or pluralities) of parallel lines in the resulting pattern on the retina. The diffractive optical element manufacturer, having calculated the desired spacing and orientation, may then pattern the surface of the optical element accordingly using, for example, a photo-resist laser. Photolithographic techniques may then be used to finish construction of diffractive optical element 105. Alternatively, holographic exposure techniques may be used to form diffractive optical element (DOE) 105.

Figure 5:
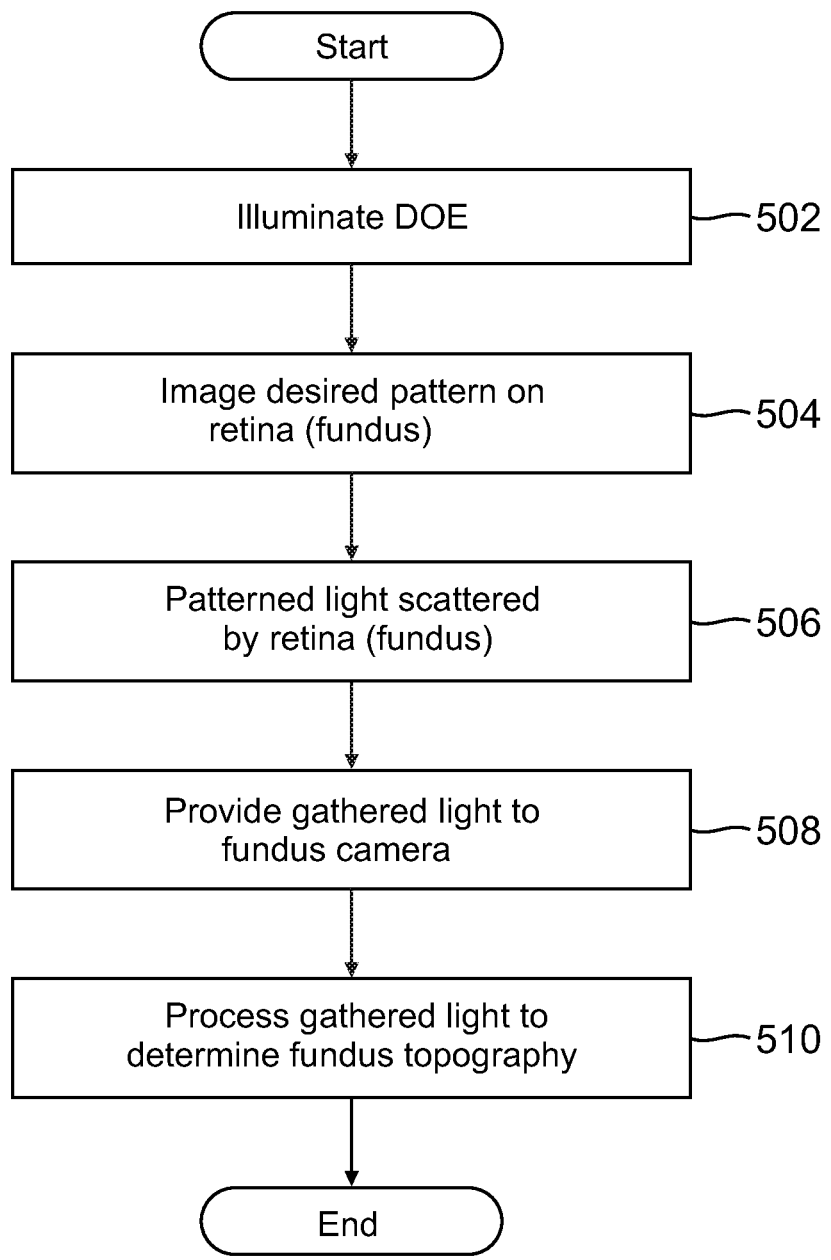
FIG. 5 is a flowchart for a method of determining retinal topography.

An example method of use for probe 100 with regard to imaging of the retinal illumination using a fundus camera will now be discussed with regard to the flowchart of FIG. 5. A clinician may first position intraocular probe 100 through a trocar cannula into the eye interior as discussed with regard to FIG. 2 and illuminate DOE 105 at 502. Advantageously, the clinician may position probe 100 to achieve the desired off-axis illumination discussed with regard to FIG. 4. DOE 105 then diffracts collimated laser beam to form the desired linear pattern on the retinal fundus at 504. The retina then reflects and scatters the resulting pattern at 506. The optics within the fundus camera may then focus the scattered light at 510 to form an image so that the fundus topography may be determined at 512. Such a determination may be made solely by the clinician. Alternatively, an image processor may process the image to determine the fundus topography. It will be appreciated that a clinician may determine the fundus topography solely from judging the projected linear pattern and without the use of a fundus camera.

While the present invention has been illustrated by the above description of embodiments, and while the embodiments have been described in some detail, it is not the intention of the applicant to restrict or in any way limit the scope of the invention to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of the applicant's general or inventive concept. It is understood that all spatial references, such as "longitudinal axis," "horizontal," "vertical," "diagonal," "top," "upper," "lower," "bottom," "left," and "right," are for illustrative purposes only and can be varied within the scope of the disclosure.

What is claimed is:

1. A pattern-generating intraocular probe, comprising:
a cannula including a diffractive optical element (DOE), the DOE being patterned such that an on-axis illumination of the DOE produces an emitted beam forming a linear pattern; and
a handpiece connected to a proximal end of the cannula; wherein the handpiece includes a laser for providing the on-axis illumination of the DOE.

2. The intraocular probe of claim 1, wherein the laser is a laser diode source.

3. The intraocular probe of claim 1, wherein the handpiece includes collimating optics driven by the laser to produce a collimated laser beam for providing the on-axis illumination of the DOE.

4. The intraocular probe of claim 1, wherein the proximal end of the cannula removably connects to the handpiece through a connector.

5. The intraocular probe of claim 1, wherein the DOE pattern is a holographic pattern.

6. The intraocular probe of claim 1, wherein the DOE pattern is a computer-generated pattern.

7. The intraocular probe of claim 1, wherein the handpiece further includes a battery for powering the laser.

8. The intraocular probe of claim 1, wherein the DOE is positioned to hermetically seal a distal end of the cannula.

9. The pattern-generating intraocular probe of claim 1, wherein the DOE is illuminated directly by the laser without use of an intervening optical fiber.

10. A method, comprising:
inserting a cannula into an eye, wherein the cannula includes a diffractive optical element (DOE) patterned such that an on-axis illumination of the DOE produces an emitted beam forming a linear pattern; and
illuminating the DOE through a lumen of the cannula so as to produce the on-axis illumination such that the emitted beam forms the linear pattern on a retinal fundus;
wherein inserting the cannula into the eve comprises holding a handpiece, with a laser to provide the on-axis illumination of the DOE, connected to the cannula.

11. The method of claim 10, further comprising rotating the cannula so as to rotate the linear pattern formed on the retinal fundus.

12. The method of claim 10, wherein the linear pattern is a grid pattern.

13. The method of claim 10, wherein the linear pattern is a plurality of parallel lines.

14. The method of claim 10, further comprising:
   imaging the linear pattern on the retinal fundus; and
   analyzing the image to determine a topography for the retinal fundus.

15. The method of claim 10, further comprising:
   manipulating the cannula through manual operation of the connected handpiece.

16. The method of claim 15, further comprising removing the cannula from the eye and removing the cannula from the handpiece.

17. An intraocular probe, comprising:
   a handpiece;
   a needle having a proximal end connected to the handpiece; and
   a diffractive optical element (DOE) sealing a distal end of the needle, the DOE being patterned to project a plurality of parallel lines onto a retina;
   wherein the handpiece include a laser for providing on-axis illumination of the DOE.

18. The intraocular probe of claim 17, wherein the plurality of parallel lines comprises two pluralities arranged to form a grid pattern.

19. The intraocular probe of claim 17, further comprising a connector for removably connecting the proximal end of the needle to the handpiece.

20. The intraocular probe of claim 17, wherein the DOE is illuminated directly by the laser without use of an intervening optical fiber.

\* \* \* \* \*